(12) United States Patent
Szasz et al.

(10) Patent No.: US 9,636,495 B2
(45) Date of Patent: *May 2, 2017

(54) FLEXIBLE AND POROUS LARGE-AREA ELECTRODE FOR HEATING

(75) Inventors: Andras Szasz, Páty (HU); Oliver Szasz, Páty (HU); Nora Szasz, Boston, MA (US)

(73) Assignee: Oncother Kft., Páty (HU)

( * ) Notice: Subject to any disclaimer, the term of this patent is extended or adjusted under 35 U.S.C. 154(b) by 692 days.

This patent is subject to a terminal disclaimer.

(21) Appl. No.: 12/863,418

(22) PCT Filed: Jan. 27, 2009

(86) PCT No.: PCT/EP2009/000597
§ 371 (c)(1),
(2), (4) Date: Jan. 19, 2011

(87) PCT Pub. No.: WO2009/092619
PCT Pub. Date: Jul. 30, 2009

(65) Prior Publication Data
US 2011/0106226 A1    May 5, 2011

(30) Foreign Application Priority Data
Jan. 27, 2008    (EP) .................... 08001487

(51) Int. Cl.
| *A61N 1/00* | (2006.01) |
| *A61N 1/04* | (2006.01) |
| *A61N 1/06* | (2006.01) |
| *A61N 1/40* | (2006.01) |
| *A61N 1/05* | (2006.01) |

(52) U.S. Cl.
CPC ............. *A61N 1/0404* (2013.01); *A61N 1/06* (2013.01); *A61N 1/403* (2013.01); *A61N 1/05* (2013.01)

(58) Field of Classification Search
CPC .... A61N 1/403; A61N 1/0476; A61N 1/0484; A61N 1/06
USPC ..................... 607/99, 100, 101, 98
See application file for complete search history.

(56) References Cited

U.S. PATENT DOCUMENTS

| 1,973,911 | A | * | 9/1934 | Ruben ........................... 607/152 |
| 4,008,721 | A |   | 2/1977 | Burton |
| 4,067,342 | A | * | 1/1978 | Burton ........................... 607/152 |
| 4,121,592 | A | * | 10/1978 | Whalley ........................ 607/98 |

(Continued)

FOREIGN PATENT DOCUMENTS

| DE | 2844980 | 4/1980 |
| JP | 11309219 | 11/1999 |

(Continued)

OTHER PUBLICATIONS

Search report for PCT Application No. PCT/EP2009/000597 issued Sep. 10, 2009.

*Primary Examiner* — Jocelyn D Ram
(74) *Attorney, Agent, or Firm* — Meyertons, Hood, Kivlin, Kowert & Goetzel, P.C.; Eric B. Meyertons (57) ABSTRACT

The present invention relates to a flexible electric field capacitive coupled energy transfer means formed from a conductive metal coated flexible material or flexible metallic net. The improved energy transfer means is flexible, porous, light and easy to manipulate treatment electrode and is used in non-invasive electrical field hyperthermia.

14 Claims, 6 Drawing Sheets

(56) References Cited

U.S. PATENT DOCUMENTS

| | | | | |
|---|---|---|---|---|
| 4,186,729 | A * | 2/1980 | Harrison | A61N 1/06 |
| | | | | 219/770 |
| 4,197,851 | A * | 4/1980 | Fellus | 607/71 |
| 4,350,168 | A * | 9/1982 | Chable | A61N 1/06 |
| | | | | 600/549 |
| 4,419,091 | A * | 12/1983 | Behl | A61N 1/044 |
| | | | | 604/20 |
| 4,785,829 | A * | 11/1988 | Convert | A61N 1/323 |
| | | | | 607/101 |
| 5,486,182 | A | 1/1996 | Nakao et al. | |
| 5,769,880 | A * | 6/1998 | Truckai et al. | 607/101 |
| 6,219,577 | B1 | 4/2001 | Brown, III et al. | |
| 6,330,479 | B1 * | 12/2001 | Stauffer | A61N 5/02 |
| | | | | 607/101 |
| 6,424,862 | B1 | 7/2002 | Brown, III et al. | |
| 6,650,922 | B2 * | 11/2003 | Kurata et al. | 600/395 |
| 7,238,196 | B2 * | 7/2007 | Wibaux | 607/96 |
| 7,627,381 | B2 * | 12/2009 | Kanzius | A61K 41/0052 |
| | | | | 607/101 |
| 7,715,921 | B2 * | 5/2010 | Palti | A61N 1/0408 |
| | | | | 607/115 |
| 7,767,936 | B2 * | 8/2010 | Ferguson | 219/219 |
| 8,019,414 | B2 * | 9/2011 | Palti | A61K 31/337 |
| | | | | 607/3 |
| 8,295,902 | B2 * | 10/2012 | Salahieh et al. | 600/374 |
| 2001/0025175 | A1 * | 9/2001 | Panescu et al. | 606/41 |
| 2002/0082668 | A1 * | 6/2002 | Ingman | 607/98 |
| 2003/0208152 | A1 * | 11/2003 | Avrahami | A61N 1/325 |
| | | | | 604/20 |
| 2004/0267190 | A1 * | 12/2004 | Tamarkin et al. | 604/20 |
| 2006/0119462 | A1 * | 6/2006 | Beens et al. | 336/200 |
| 2008/0072052 | A1 * | 3/2008 | Suzuki | 713/176 |
| 2008/0161889 | A1 * | 7/2008 | Paul et al. | 607/102 |
| 2011/0208182 | A1 * | 8/2011 | Szasz et al. | 606/33 |
| 2012/0310311 | A1 * | 12/2012 | Elkah | 607/102 |
| 2013/0274841 | A1 * | 10/2013 | Eckhous et al. | 607/101 |

FOREIGN PATENT DOCUMENTS

| | | |
|---|---|---|
| JP | 2001046520 | 2/2001 |
| SU | 1771759 | 5/1990 |
| WO | 2004030760 | 4/2004 |

* cited by examiner

FLEXIBLE AND POROUS LARGE-AREA ELECTRODE FOR HEATING

BACKGROUND OF THE INVENTION

1. Field of the Invention

The present invention relates to inventive flexible applicators for electric field capacitive coupled energy transfer or for simple heating by current flow through means formed from a conductive metal coated flexible material. The improved energy transfer means is a flexible, porous, light and easy to manipulate treatment electrode.

2. Description of the Relevant Art

Heating is widely applied in many areas of medicine and also used for cosmetic treatments. For example Radiofrequency/microwave hyperthermia devices can be used to force energy absorption in tissue to cause damage to unwanted structures and/or increase the temperature of a targeted area above the normal body temperature. One use of hyperthermia devices is the treatment of cancer. In the case of cancer treatment, tumor cells are more sensitive to stresses, for example, heat and/or electromagnetic fields and chemical treatments, than the surrounding normal tissue cells. Therefore the aim is to pump sufficient energy to the tumor tissue to irreversibly damage the tumor cells, but which can be tolerated by normal tissue cells. Another use for hyperthermia devices is to increase temperature and blood circulation for cosmetic (fat-burning, lipid-distortion, shape-correction, etc), dermatological and pain relief treatments.

Conventional non-invasive electrical field hyperthermia devices commonly use as an energy transfer means two bolus electrodes placed on opposing sides of the target tissue to be heated. Other non-invasive hyperthermia solutions use radiative antennas or phase-array set of antennas to pump the desired energy into the requested area, cooling also the immediate surface by water-bolus application. Other solution could be the direct heating of the applicator to reach the desired temperature directly on the skin surface. These arrangements are optimized to deliver energy to a small target area and is not suitable for the treatment of a large target area.

For example WO 2004/107816 A discloses an apparatus of flexible and "breathable" electrical heater which is heated up independently, and heats up the underneath skin by heat diffusion. The device is also useful for drug delivery of heat-liberated drugs on the skin.

U.S. Pat. No. 4,164,226 centers on the iontophoretic effects with unidirectional (DC) current. No capacitive coupling with continuous AC/RF is disclosed in U.S. Pat. No. 4,164,226 where the load is a complex impedance of the treated body part.

WO 99/52424 A discloses a typical intraluminar applicator which it not suitable for treating the outer surface. The applicator is based on DC or pulsed DC current, having iontophoretic or electroporation effects.

WO 00/47274 A is directed to an apparatus for iontophoretic or electroporation applications. The applicator is flexible and the invention is in its topological solution. This type of treatment performed with the applicator of WO 00/47274 A has direct contact with high voltage and low current (microamperes), while the applicator of the present invention is for RF conduction having under 100 V and high current (Amps).

U.S. Pat. No. 5,486,182 discloses an apparatus for intralu-minar and/or intracavital electro-cauterization (ablative electric burn). This apparatus and the method performed with such apparatus is directly an inside application (like in WO 99/52424 A) and the cauterization made by inside mechanical cage to remove the polyp.

None of the prior art literature describes an applicator for RF conduction having under 100 V and high current for generating heat inside the body, while the energy-absorption is caused by the RF-current which flows through the body and makes the heating in-situ deep. The device of the present invention applies continuous AC or RF, high current low electric field for the deep heating of tissue which is not disclosed in the afore-mentioned prior art documents.

SUMMARY OF THE INVENTION

The electrode geometry and arrangement, in an embodiment, are optimized to achieve the optimal temperature, Specific Absorption Rate (SAR) and electric field distribution for a given application. One of the most important practical parameters of the electrode is the flexibility of the electrode and the ability of the electrode to conform to the shape of the application area. Due to the water-bolus and the relatively complex mechanical construction the available set of electrodes does not fit to all the shape-request in practical applications, there are rather limited number of the available electrode-shapes compare to the individual requirements. Also important is the cooling of the electrode/applicator to prevent burning of the application area and to maintain patient comfort during treatment. Various technical solutions are applied in the field of hyperthermia, however a porous electrode/applicator having excellent flexibility is lacking.

Herein, as an example of the application, we report the development of a flexible electromagnetic energy transfer means, preferably an electric field capacitive coupled energy transfer means and methods for its use. This is achieved by providing a flexible, porous, light and easy to manipulate electrode system for capacitive heating that can be constructed to be applied to a large surface area. The conductive electrode material is a conductive metal coated flexible material which can easily conform to the contours of any application area and that allows the exchange of heat and fluids through the material. The flexible electromagnetic energy transfer means or flexible electric field capacitive coupled energy transfer means and method can be used for medical and cosmetic treatments as well as for welding, soldering and gluing purposes and for keeping any liquids or fluids such as dielectric materials warm. Temperatures of up to 50° C. can be reached using the electromagnetic energy transfer means.

The prior art embodiments mostly deal with deep heating and with energy delivery by radiofrequency currents. Most of the prior art documents apply DC current, having definitely different effect and treatment facilities than the RF-applicator, i.e. the electromagnetic energy transfer means of the present application. Almost all of the prior art methods treat the very surface area, keeping the energy at the skin (or internal surface) region and limit their action on the surface treatment. Moreover, many of the prior art embodiments deal with electroporation, a high-voltage pulse treatment to make the cellular membrane bubbling, regulate their permeability or destroy them, as well as to support the drug-iontophoretic delivery with a force-full penetrating tool. However, the prior art literature does not disclose the use of capacitive coupling and capacitive coupled electrodes in the meaning like a capacitor in a high frequency circuit. The electromagnetic energy transfer means of the present invention applies a low electric field with high current and continuous AC or RF supply. Almost all of the prior art documents apply high electric fields, low current and pulsing DC.

The term "electromagnetic energy transfer means" as used herein refer preferably to a capacitive coupled and/or radiative coupled and/or conductive coupled energy transfer means.

The term "means" as used herein refers to an applicator for hyperthermia purposes, an applicator for magnetic and/or electric field applications, an electrode, a metallic net or a metallic network, or to flexible textile or textile-like structures comprising at least one metallic coating so that this textile or textile-like structure can be used as applicator or electrode.

The prior art does not disclose the electric field capacitive coupled energy transfer means that is flexible, porous, light and easy to manipulate and can be applied to large areas.

Also the flexible, porous and shape-adopting applicators are missing for the other hyperthermia solutions also. The U.S. Pat. No. 6,330,479 discloses a flexible radiative microwave applicator comprising a flexible dielectric fluid containing compartment on the surface of the applicator facing the treatment area and an antenna array on the opposite surface. Thus although flexible energy transfer means are known in the prior art, an energy transfer means having the structure and advantages of the present invention is not disclosed in the prior art.

U.S. Pat. No. 6,330,479 discloses a microwave garment for heating and/or monitoring tissue comprising an electromagnetic energy transfer means for directing energy to a target tissue.

However, there are basic differences between the embodiment of U.S. Pat. No. 6,330,479 and the present invention. U.S. Pat. No. 6,330,479 is a microstrip antenna arrangement, while the present embodiments use capacitive coupling. U.S. Pat. No. 6,330,479 is a microwave radiative solution, that means, not any current goes through the patient, only the absorption is used. Thus, the patient is not part of the complete arrangement, the patient is only a passive absorber of the radiation. In the present embodiments, the current flows through the patient, the absorption is the active current energy (not the radiation), so that the patient is a part of the electronics, i.e. is a part of the complete arrangement and not only a passive absorber.

Since U.S. Pat. No. 6,330,479 discloses a microwave antenna arrangement there is no need for a counter-electrode when the embodiment is a condenser arrangement including a RF-electrode and a counter electrode. The electrode of U.S. Pat. No. 6,330,479 is not a condenser electrode and the electrode is not equipotent. The microstrip antenna as described, for instance, in U.S. Pat. No. 6,330,479 is constructed for radiation and its main task is, to generate a definite mixture of electric and magnetic fields (according to the Maxwell equations it radiates $S=E\times B$ energy-flow (the well known Poynting vector). The radiated wave leaves the antenna and the system and is adsorbed in the target. In some embodiments the target is a part of the electronic circuit, a definite RF-current (not wave-radiation as it is in the radiative application) flows through the target between the two (actually always oppositely charged) electrodes. In the antenna arrangement of U.S. Pat. No. 6,330,479 the heating is mainly the well-known Joule-heat, which is proportional by the square of the current, and originated from the impedance loss (depolarization loss and resistivity loss). In some embodiments the radiative component is eliminated as much as possible, and only the conductive behavior of the matter (electric field alone) is used. Therefore focusing of the heat generated during treatment can be much better achieved with the electrodes than with the antenna arrangement. In cancer treatment it is important to selectively heat the tumor and not the surrounding healthy tissue in order to destroy the tumor cells. If the tumor is not selectively heated and the surrounding healthy tissue is preferentially heated, such a treatment will support tumor growth due to the increased provision of nutrients to the tumor tissue.

The above described technical differences of the embodiments described herein, in comparison to the embodiment of U.S. Pat. No. 6,330,479, have the following effects which are tightly connected to both embodiments.

The antenna arrangement of U.S. Pat. No. 6,330,479 consists of a mosaic of antennas which necessarily require a well calculated impedance fitting for all the antennas. This makes the arrangement of U.S. Pat. No. 6,330,479 more complicated than the one of the present invention which does not need any impedance fitting.

Moreover as shown in FIGS. 1B, 8, 9, 10 and 11 of U.S. Pat. No. 6,330,479 a big bunch of cables is needed in order to connect all the single antennas of the antenna arrangement which increases the costs for manufacturing such a device, decreases the patient's comfort when wearing said device and increases the susceptibility to damage and the fault liability. In contrast, the arrangement of the embodiments described herein only required a single cable for connecting the RF-electrode and the counter-electrode to the radiofrequency source (RF source).

In other words, the capacitive calculation uses the 50 Ohm nominal impedance for the full situation (i.e. for the impedance-matching) while U.S. Pat. No. 6,330,479 must make this matching in every single mosaic part, i.e. in every single antenna of the mosaic arrangement of antennas, taking due care about the cross couplings and interferences between the single antennas in order to provide a well adjusted and suitable treatment to the patient. Such complications which are really difficult to handle and to adjust or to balance are avoided in the arrangement of the described embodiments, since these embodiments do not use a plurality of single antennas in a certain arrangement. The described embodiments make use of an equipotent RF electrode and counter electrode without the need of any impedance-matching and without any occurrence of cross couplings and interferences.

A radiative arrangement like this of U.S. Pat. No. 6,330,479 is not able to focus with a single source, i.e. with a single antenna. It is necessary to radiate from various angles by various energies to make a focus in the target. In the solution of the described embodiments, the RF-current flows on the easiest pathway which possible for it. The easiest pathway goes through the low impedance volumes, which automatically chooses in this way the intensively metabolizing malignant volumes. Consequently, focusing the generated heat on the diseased tissue and simultaneously reducing the risk of burns in the healthy tissue is much easier and more precisely achieved by the arrangement of the embodiments described herein than with the arrangement of U.S. Pat. No. 6,330,479. Furthermore, the embodiments of U.S. Pat. No. 6,330,479 might have an advantageous wearing comfort for the patient in comparison to embodiments with common heavy and flat bolus electrodes. However in comparison to the energy transfer means of the embodiments described herein, the microwave applicators of U.S. Pat. No. 6,330,479 are heavy due to their water cooling system which is part of the applicator, complicated to wear due to the extensive cabling and must fit quite exactly to the body part to be treated which requires a whole set of applicators in various sizes of forms for the different body parts such as, head, leg, arm, breast, abdomen etc.

The microstrips of the embodiments of U.S. Pat. No. 6,330,479 are coax-cable connected (both the ground or the counter-line and the active (also called hot line) are introduced to the applicator. In the embodiments described herein, the ground electrode and the hot-line is connected to different applicators, (in symmetric case two actually oppositely "charged" electrodes make the capacitor, in asymmetric case one of them is grounded (counter electrode). Further asymmetry could be introduced by size differences of the capacitive electrodes also. Every applicators are equipotent in their all surface.

Figure 1:
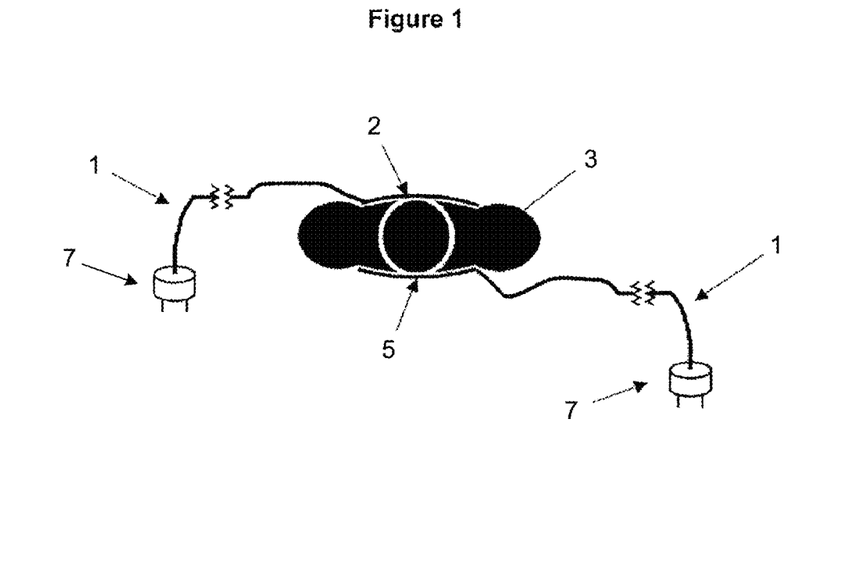
FIG. 1 shows an example of a flexible sheet electrode applied to the uneven surface of the patient's body; it shows geometrically symmetric arrangement, but that could be geometrically asymmetric as well, when the sizes of the electrodes are not identical; the electrodes (both the geometrically symmetric or asymmetric) could be electrically also symmetric (oppositely charged electrodes alternating by the applied frequency) or asymmetric, (having one electrode grounded, and the other one changes its polarity by the frequency)

The term "electrode" as used herein refers to one of the at least two electrodes of the condenser or the capacitor or to a single electrode which could be heated by the current flow like a hot plate. These electrodes are called RF-electrode, capacitive electrode, counter-electrode or simply electrode. The condenser arrangement as shown in FIG. 1 can be geometrically symmetric if the two electrodes have the same size or geometrically asymmetric if the two electrodes do not have the same size. Moreover, the electrodes can also be electrically symmetric if they are oppositely alternating charged by the applied frequency or they can be electrically asymmetric if one electrode is grounded and the other one changes its polarity by the frequency.

An advantage of the energy transfer means of the embodiments described herein is that a complicated cooling system and complicated cooling procedure and measuring and adjusting of cooling is not required at all. The RF-electrode as well as the counter electrode is one single large electrode, having uniform voltage on it and having a single cable used only for the electric connection to the RF-source. This is a really light and comfortable to wear device which easily follows the body contours without the need that the RF-electrode or counter-electrode itself has the exact form of the respective body contour.

In an embodiment the counter-electrode is opposite to the RF-electrode and the patient or the body part of the patient which is in need of treatment is located between the RF-electrode and the counter electrode so that the current flow goes through the diseased tissue, for instance, the cancerous or malignant tissue.

Thus, the applicators for electric field capacitive coupled energy transfer is a closed circuit comprising the RF-source, the RF-electrode and the counter-electrode connected each by a single cable to the RF-source. The RF-electrode and the counter electrode form a condenser where the patient in between the two electrodes is part of the circuit in form of a dielectric.

The microwave antennas of the applicator of U.S. Pat. No. 6,330,479 must be isolated by their DC conduction from the skin and require circulated water for the good transmission (see FIG. 5 in U.S. Pat. No. 6,330,479, especially the parts "circulating water port", "water bolus outlet", "water bolus inlet", "thermal mapping channels", "5 mm thick circulated water bolus", "5 mm water bolus" and FIG. 7 especially the parts "8 thermal mapping sensors", "water coolant", "temperature controlled water bath", "thermal mapping system" etc.).

Two remarkable advantages of embodiments of the applicators are the fully missing of any isolators, so that the applied voltage could remain low without absolute no hurting for patient while in addition no cooling system is required and still a safe heating of the diseased tissue can be performed without the need of any cooling system.

As mentioned above, the antenna arrangement of U.S. Pat. No. 6,330,479 has to be well fitted for the actual application in order to correctly heat the diseased tissue, avoid burning of the skin or not diseased tissue and to well apply the cooling system of the arrangement, which makes complications in the production of the applicator required several different forms and sizes and makes the production quite cost intensive.

In comparison to that, the production of the applicator described herein is easy and simple, since the RF-electrode and counter-electrode each include one piece of a homogeneous flexible material which is used as a simple condenser-plate and not like an antenna.

The fabrication of the electrode of the present invention is done in the simple continuous coating of the given flexible material in a large area (e.g. measured as 100 $m^2$ in a roll). One has only to tailor the coated materials for the actual body shape like confectioning. In contrast, the antenna arrangement of U.S. Pat. No. 6,330,479 has a complicated fabrication due to the special mosaic form and the even more special (and electronically matched) strip-geometry (see FIG. 1A of U.S. Pat. No. 6,330,479) which is complicated to produce.

These remarkable differences and remarkable advantages of the embodiments described herein in comparison to the embodiment of U.S. Pat. No. 6,330,479 demonstrate that the embodiments described herein are not only an alternative applicator addressing similar indications is disclosed in U.S. Pat. No. 6,330,479 but also eliminate several drawbacks of the embodiment of U.S. Pat. No. 6,330,479 in a non-obvious manner.

It is the object of the embodiments described herein to provide an energy transfer means for transferring heat through an uneven, fractal and/or percolative surface to a target tissue in a focused manner, avoiding burning of the healthy tissue and increasing wearing comfort of the means for the patient during treatment.

The object is solved by the teaching of the independent claims disclosing an electromagnetic (e.g. capacitive, radiative or conductive) energy transfer means formed from a conductive metal coated flexible material that is flexible, light, porous and easy to manipulate. Further advantageous features, aspects and details of the invention are evident from the dependent claims, the description, and the examples of the present application.

BRIEF DESCRIPTION OF THE DRAWINGS

Advantages of the present invention will become apparent to those skilled in the art with the benefit of the following detailed description of embodiments and upon reference to the accompanying drawings in which.

While the invention may be susceptible to various modifications and alternative forms, specific embodiments thereof are shown by way of example in the drawings and will herein be described in detail. The drawings may not be to scale. It should be understood, however, that the drawings and detailed description thereto are not intended to limit the invention to the particular form disclosed, but to the contrary, the intention is to cover all modifications, equivalents, and alternatives falling within the spirit and scope of the present invention as defined by the appended claims.

DETAILED DESCRIPTION OF THE PREFERRED EMBODIMENTS

Figure 6:
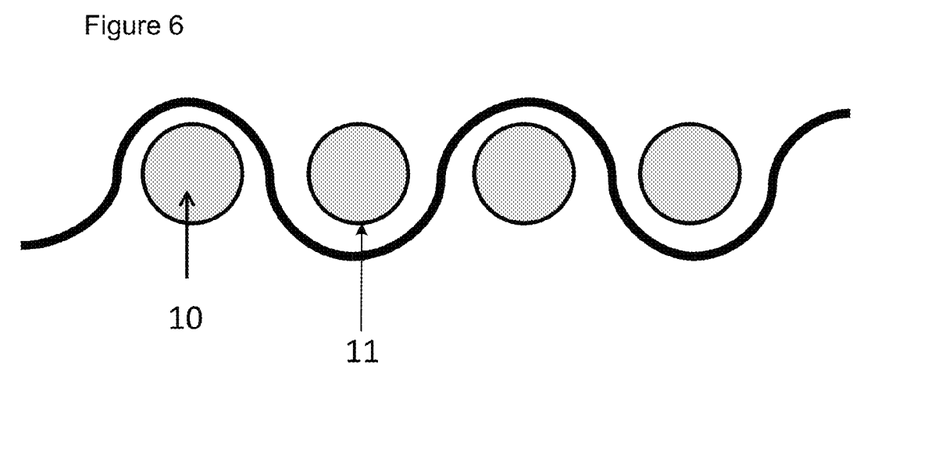
FIG. 6 depicts a cross-sectional view of a coated fiber mesh.

Embodiments described herein are directed to an electromagnetic energy transfer means for directing energy to a target, wherein the energy transfer means includes at least one conductive metal electrode material, wherein at least one conductive metal electrode material layer is coated onto the surface of a flexible carrier, and wherein the coated flexible carrier is porous and allows the movement of water through the coated flexible carrier. Thus, the coated flexible carrier is an electrode of the electromagnetic energy transfer means and the complete electrode is porous, flexible and allows the movement of water through said electrode. FIG. 6 depicts a cross section view of a coated flexible carrier. Flexible carrier 10 is coated by a metal coating 11.

Figure 7:
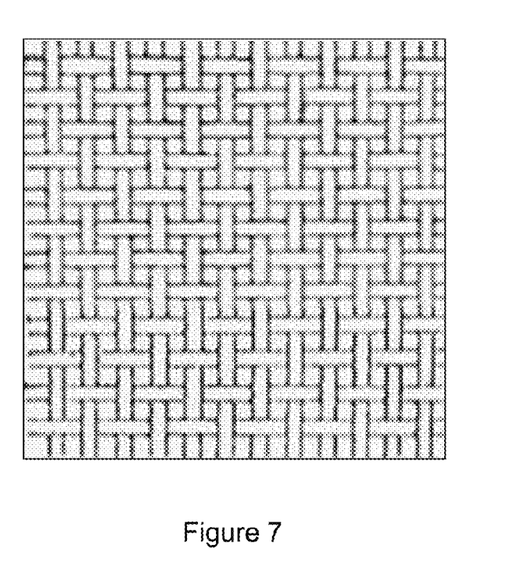
FIG. 7 depicts a top view of a metallic net having a woven structure of metallic fibers.
Figure 8:
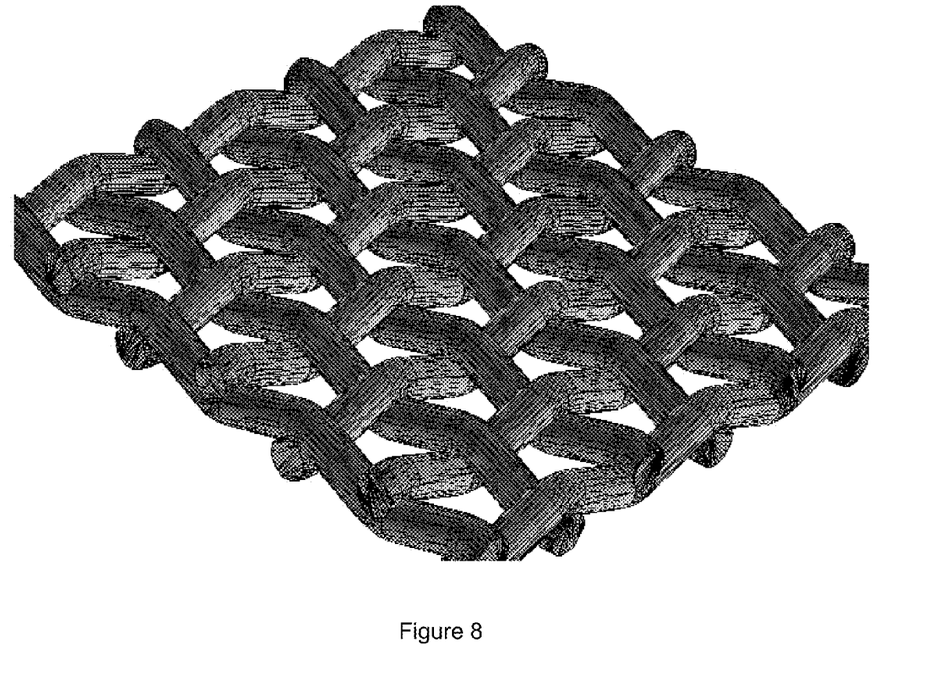
FIG. 8 depicts a perspective view of a metallic net having a woven structure of metallic fibers.
Figure 9:
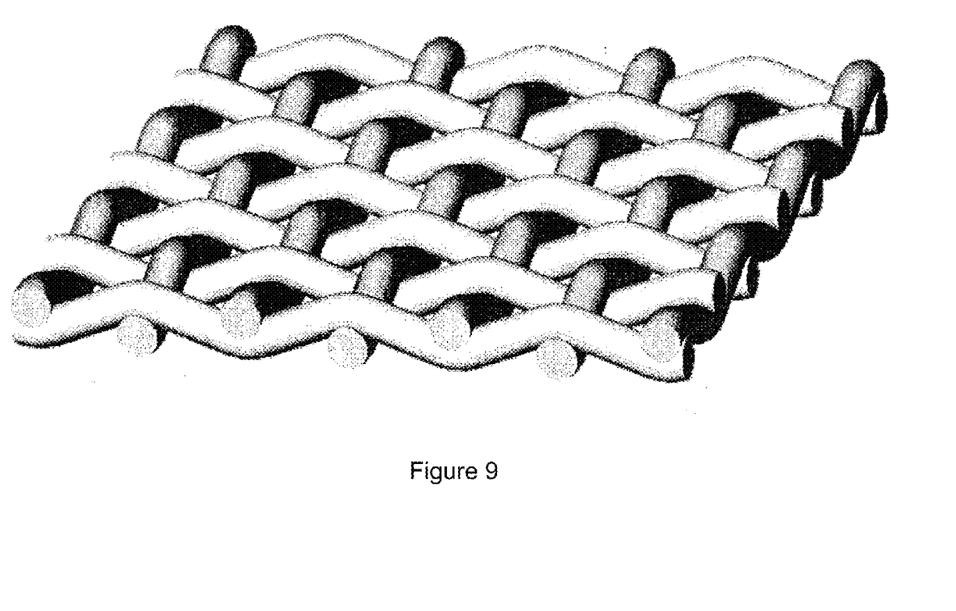
FIG. 9 depicts an alternate perspective view of a metallic net having a woven structure of metallic fibers.

Instead of a coated flexible carrier or a coated flexible material, a conductive metallic net or a conductive metallic network can be used, manufactured of at least one conductive metal electrode material. Exemplary conductive metallic nets are depicted in FIGS. 7-9. Such metallic nets or metallic networks do preferably not comprise any backbone such as a polymeric network structure. The metallic net or network is preferably a woven structure of metallic fibers having very similar properties as the coated flexible material such as a coated textile. The conductive metallic net or network is flexible, allows water and other fluids as well as gases to move through it, can be folded without negative effect concerning conductivity and is able to cover uneven, fractal and/or percolative surfaces. Consequently all kind of metallic nets and networks having the afore-mentioned properties of the conductively coated materials such as the conductively coated textiles are useful within the electromagnetic energy transfer means.

Thus the means for transferring electromagnetic energy, which is mainly heat, includes a carrier or support or material which is coated with at least one conductive metal electrode material or conductive metal electrode material layer. This means or this electrode of this means is suitable to heat up a target such as a liquid or body tissue of a mammal, a culture plate, a dielectric fluid or a tissue sample or a biopsy to up to 50° C. and normally up to 45° C. to 48° C.

The carrier or support or material and especially the solid carrier or solid support or solid material is made of plastic, polymers or natural substances such as biopolymers and is coated with a conductive material such as a conductive metal or metal alloy. Moreover said coated carrier or coated support or coated material is porous and allows a liquid to pass through said carrier or support or material. Furthermore, the coated carrier or coated support or coated material is flexible, i.e. does not have a definite or predefined shape and is able to follow the uneven curvatures of the human or animal body or any cavity containing liquids, fluids, gas or solid substances which should be heated up.

The term "porous" as used herein refers to the ability that the coated carrier or coated support or coated material allows water and any gas to move through said coated carrier or coated support or coated material. The pore size can be up to 0.1 mm or even larger. Consequently, the energy transfer means includes one or two electrodes which are flexible, electrically conductible and permeable or penetrable for aqueous liquids, water and gases.

The energy transfer means includes a flexible porous material, carrier or support coated with conductive metal so that the energy transfer means acts like an radiative antenna or could be heated up alone by the current-flow through it. The energy transfer means can be used for radiative microwave treatment and is also applicable in a phase-array arrangement.

A porous textile is suitable as the flexible material or flexible carrier or flexible support however any porous material having flexibility similar to the flexibility of a woven or non-woven textile could also be used. Thus any kind of textile, woven textile, non-woven textile and even non-textile material is suitable as flexible porous material. Such a flexible porous material can also be named as a flexible porous solid support or flexible porous solid carrier. Such materials, carrier or supports are not limited by a specific shape and have the consistency and/or texture of piece of textile or a piece of fabric or drapery. Consequently all known natural and artificial materials such as polyamide (Nylon®), poly-∈-caprolactone, poly-para-dioxanones, polyanhydrides, polyhydroxymethacrylates, fibrin, polyetherester, PEG, poly(butylene terephthalates), polycarbonates, poly(N-vinyl)-pyrrolidone, polyvinylalcohols, polyesteramides, polyethyleneoxide, polypropyleneoxide, polyurethanes, fibrinogen, starch, collagen, zein, casein, β-cyclodextrins, polyacrylates, polyacrylamide, polyimides, polyethylene, polypropylene, polytetrafluoroethylene, fluorosilicones, rayon, polysulphones, silicones, polysiloxanes, polyvinyl halogens and copolymers or mixtures of these substances.

Preferred are materials, carrier or supports such as these mentioned before which provide a good adhesion for the metallic coating. Also preferred are materials, carrier or supports which are manufactured of or which include a plurality of single fibers like a woven textile wherein one set of the single fibers extends along the complete length of the textile more or less in a substantially parallel manner while the other set of fibers is arranged in a substantially parallel manner diagonal to the first set of fibers. Thus fibers having a length which is similar to the length of the textile comprising said fibers are preferred.

In a further embodiment the single fibers of the material, carrier or support are coated like a tube that means not only a part of the surface of the fiber is coated rather the coating is applied all around the fiber.

Moreover it is preferred that such material, carrier or support is percolative and/or fractal or has a percolative and/or fractal structure without any discontinuity between the in and out cables of the electromagnetic energy transfer means. In other words, the metallic nets or the coated carriers are such flexible that they are able to cover uneven, fractal or percolative surfaces or they are able to follow the structure of uneven, fractal or percolative surfaces.

The conductive metal coating is a multilayer coating. Preferably one of the layers is silver which has a good antibacterial effect and provides for good radiofrequency (RF) conduction. Moreover silver has an anti-odor effect together with moderate anti-perspiration activity. This makes silver preferred for cosmetic, medical and well-being applications.

However other conductive metal coatings can also be used. The resulting conductive metal coated flexible material is still sufficiently porous to allow for the exchange of heat and fluids, especially aqueous solutions, water and sweat or perspiration. Preferably the electroless (autocatalytic) deposition of the conductive metal coating is used which is one of the most frequently used methods for fabricating coatings for corrosion- and wear-resistant purposes.

The textile can be coated by extra plastic layer for galvanic isolation. This should preferably not be a continuous layer, but a layer on the fibers only in order to keep the porous structure free and open. If the device is double isolated, direct metallic contact could be used. The multilayer structure coats the fibers co-axially and perfectly continuous. If the metal layer-making technology is dipping electroless process than the crossing of individual fibers could be also perfectly coated individually fiber by fiber, if it is galvanic, then the crossings could be coated only as a cross, not keeping the individual fibre co-axial structure. The plastic coating however has to be dipping with such surface tension of the bath, which does not allow the isolation of the metallic coated fibers at their crossing, only coats their outer surface, however the coating does not fill up the pores so the material remains porous.

Ideally treatment electrodes or applicators as energy transfer means are required that are suitable for application to all parts of the human body. For this reason there is a need for a flexible electrode/applicator that can conform to the contours of the body. The coated flexible carrier or the flexible metallic net acts as an electrode for the treatment of a large and/or uneven, fractal and/or percolative surface while these carriers or metallic nets can easily be fixed on said surface via a bandage, weights, springs, rubbers or most preferably by means of magnetic fixing using small magnets, magnetic clips or the like.

The flexible electric field capacitive coupled energy transfer means is able to fulfill this requirement, i.e. to be conductive, flexible, foldable, porous and able to cover uneven, fractal and/or percolative surfaces smoothly like a cloth following the contour of the surface. The energy transfer means is formed from a conductive metal coated flexible material or a metallic network that can be folded or formed freely even into cylinder. Thus the energy transfer means can conform to gradual and sharp curvatures. For example, in the case of sharp curvatures it can easily conform to the shape of a limb by wrapping around the limb or can conform to the shape of the skull. Alternatively, in the case of gradual curvatures it can conform to the shape of the torso.

Also the flexible electromagnetically coupled energy transfer means is lightweight and therefore can be produced to cover a large area, such as the torso, without causing patient discomfort due to excessive weight of the energy transfer means. This allows the treatment of large areas in a single treatment session. Also the flexibility of the energy transfer means allows for good contact between the energy transfer means and a large application area, for example, the torso.

The flexible electromagnetically coupled energy transfer means is also porous. This allows for natural cooling of the treatment area due to exchange of heat through the energy transfer means via convection. Also a simple external air cooling system, for example a directed air flow from a fan, can be used to cool the application area to prevent burning and maintain patient comfort. As a result there is no requirement for a complicated fluid cooling system as is the case in conventional bolus electrodes. This allows for a simple and lightweight construction with low maintenance costs.

The porosity of the energy transfer means also allows for the exchange of fluids through the energy transfer means. Thus perspiration can evaporate naturally through the porous energy transfer means and therefore increase patient comfort. Conversely the porosity of the energy transfer means allows the application of liquid treatments.

Due to the simple construction of the flexible energy transfer means it could be provided as a single use disposable electrode or could be produced to specification for an individual patient.

A further advantage of the flexible energy transfer means is that there is no requirement for a bulky, rigid-frame and difficult to operate bolus electrode applicator. Also the flexible energy transfer means can be used in place of the conventional bolus electrode applicator with conventional hyperthermia devices.

However the flexible energy transfer means could also be used as a detachable application "pad" attached to the patient contact area of conventional hyperthermia applicators.

The flexible energy transfer means requires no isolation or only a very low level of isolation, so the overall impedance of the system is low. Therefore with the flexible energy transfer means in comparison to a conventional bolus electrode the use of the same power produces a higher current, which is of course optimal for heating.

Also the use of a thin metallic layer in the flexible energy transfer means or a thin metallic network as the flexible energy transfer means makes it more suitable for the inductive part of the capacitive coupling. This provides a significant advantage as one of the main problems in capacitive coupling is the fact that no inductivity exists in the system for the optimal coupling and the external impedance wastes a large part of the power.

Until now, hard, inflexible, heavy and relative small electrodes preferably bolus electrodes were used for the present purpose. The described embodiments replace these inconvenient, inflexible and heavy electrodes used for non-invasive electrical field hyperthermia by flexible, thin, porous and if needed large electrodes or electromagnetic energy transfer means which fit to the contours of a human or animal body, are light, allow the passage of water or other liquids such as perspiration and have the same or a similar conductivity as the conventional electrodes. The term "similar conductivity" refers to at least 80%, preferably at least 90% of the conductivity of a conventional bolus electrode used for this purpose.

Thus the described embodiments are directed to an electric field capacitive coupled energy transfer means for directing energy to a target tissue of a mammal, the electric field coupled energy transfer means comprising conductive metal electrode material, wherein at least one conductive metal electrode material layer is coated onto a sheet of flexible material, and wherein the coated sheet of flexible material is porous. Instead of the coated flexible material a metallic net or a network of metallic fibers can be used.

The flexible material is usually polypropylene or polyamide. Polyurethane or other plastics as well as the above mentioned materials are also suitable. The flexible material has woven or non-woven structure. Textiles made from natural fibers (cotton, wool etc.) have normally too short fibers with rough surfaces, so their specific surface is too large to coat it effectively with something. The coated layers could be any metals, which due to the better adhesion generally made by various metallic layers subsequently added on to each other. Both the galvanic and the dipping (electroless, chemical) processes has to start with a catalytic preparation (generally platinum and/or its compounds) and the coating process continued afterwards. The electroless is autocatalytic, so generally nickel salts such as nickel-phosphorous (Ni—P compounds, $H_3PO_2$, $H_3PO_3$, $H_2PO_2^-$, $H_2PO_3^-$), nickel phosphate and/or nickel-boride compounds are applied first, and other better conductive layers (copper- and/or silver-, sometimes gold-alloys) afterwards, on their top. No special preference of the layers exists; only requests of their electrical and mechanical properties could be described. Electrically we request good conductors, preferable copper silver, etc. mechanically we prefer as stable as possible in combination with flexibility as high as possible. Its sew-ability is also a preference.

Furthermore, embodiments described herein relate to a thermotherapy device or hyperthermia device or non-invasive electrical field hyperthermia device including the electromagnetic energy transfer means. Such device is used in hyperthermia especially capacitive electro-hyperthermia and most preferably for large surface areas of the human or animal body.

The hyperthermia device or arrangement or hyperthermia arrangement includes a condenser and a radiofrequency source (RF source).

Concerning the radiofrequency source there is no limitation. Any common radiofrequency source can be used as long as the radiofrequency source is able to provide radiofrequency fields in the range of preferably 10 kHz to 50 MHz, and could be safely controlled according to the treatment demands. The range of frequencies supplied can actually be from below detectable the limit (effectively measured as 0 MHz) to 500 MHz, preferably from 10 kHz to 100 MHz, more preferably from 10 kHz to 45 MHz and most preferably 13.56 MHz or any value obtained by multiplication or division by an integer, preferable division by 40. Thus, the following frequencies are most preferred: 13.56 MHz, or $\frac{1}{100}$, $\frac{1}{40}$, $\frac{1}{20}$, $\frac{1}{10}$, $\frac{1}{2}$ times, 2 times or 3 times, etc. this value of 13.56 MHz (i.e. 6.78 MHz, 27.12 MHz or 40.68 MHz). The low frequencies are preferred to make definite conduction conditions instead of the radiation of the tissue which easily causes burns in the treated tissue and especially on the skin where the radiation antenna arrangement is adhered or attached to so that controlled cooling like water cooling is necessarily required in such a radiation arrangement.

When the current flows through the patient, we use RF (preferable 13.56 MHz); when the current flows through only the net or only the coated carrier, we can use what we want, but most practical is 50 Hz, low (2-3 V) voltage.

FIG. 1 depicts an example of a hyperthermia device. The condenser of the hyperthermia device includes at least one electrode 2, which is also called RF-electrode, and at least one counter electrode 5 which are arranged or positioned in opposite to each other on the patients skin with the patient 3 in between the at least two electrodes so that the patient becomes part of the condenser when the current goes through the patient and through the diseased tissue which is in need of treatment and which is of course also located in between the RF-electrode and counter electrode. An electrode cable 1 is coupled to each electrode and includes a plug 7 which is used to couple an electrode to a power source. FIG. 1 shows geometrically symmetric arrangement, but that could be geometrically asymmetric as well, when the sizes of the electrodes are not identical. The electrodes (both the geometrically symmetric or asymmetric) could be electrically also symmetric (oppositely charged electrodes alternating by the applied frequency) or asymmetric, (having one electrode grounded, and the other one changes its polarity by the frequency).

Figure 2:
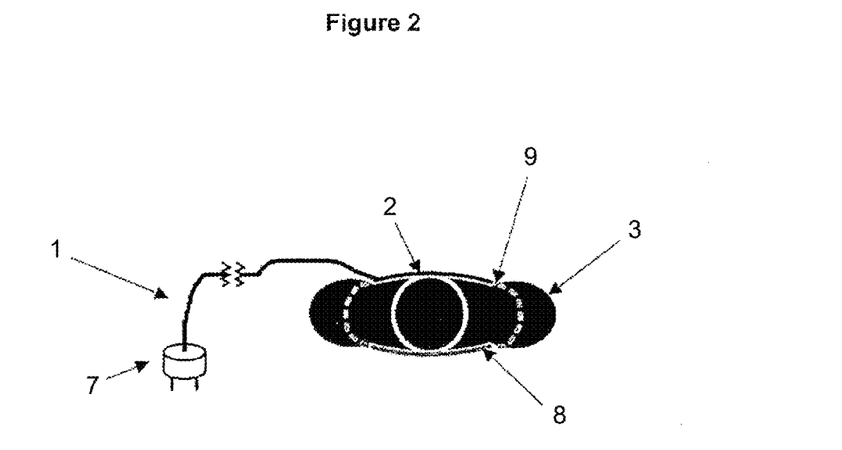
FIG. 2 shows an example of a flexible sheet electrode when applied to the uneven surface of the patient's body indicating different means for fixing the flexible sheet electrode; this case shows the arrangement, when the metal net or the conductive metal coated flexible carrier is heated by the current flowing through the net (not through the patient) and the heated net heats up the patient (like any hot plate does)
Figure 3:
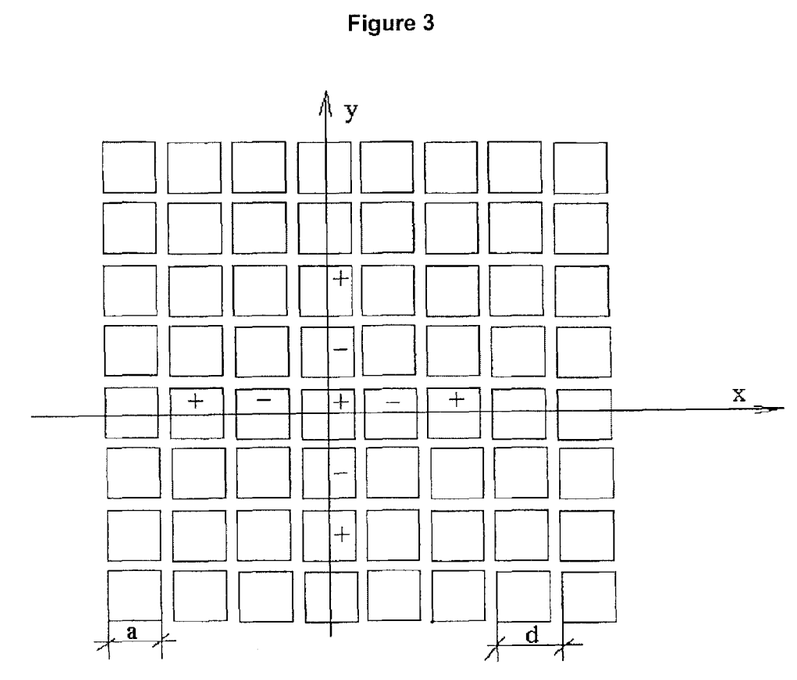
FIG. 3 shows a matrix (chess) arrangement of alternating positive and negative electrodes.
Figure 4:
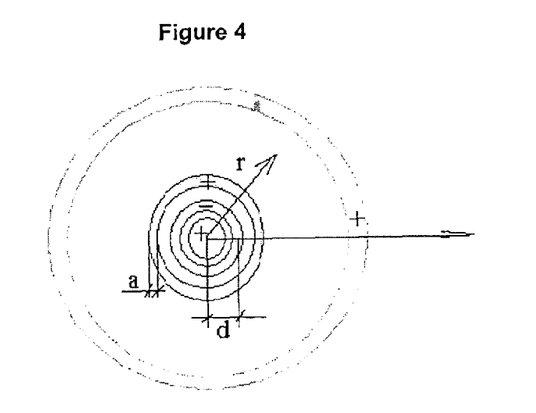
FIG. 4 shows a concentric ring arrangement of alternating positive and negative electrodes.

FIG. 2 depicts an alternate example of a hyperthermia device. The condenser of the hyperthermia device includes at a single electrode 2, which is also called RF-electrode. Counter electrode 5 is absent from this embodiment, and is replaced by a rubber pad 8, so that the patient 3 is positioned between electrode 2 and rubber pad 8. In this embodiment, electrode 2 is heated by a current flowing through the electrode (not through the patient). The heated electrode 2 imparts heat to the patient (similar to a resistive heater). An electrode cable 1 is coupled to electrode 2 and includes a plug 7 which is used to couple the electrode to a power source.

Figure 5A:
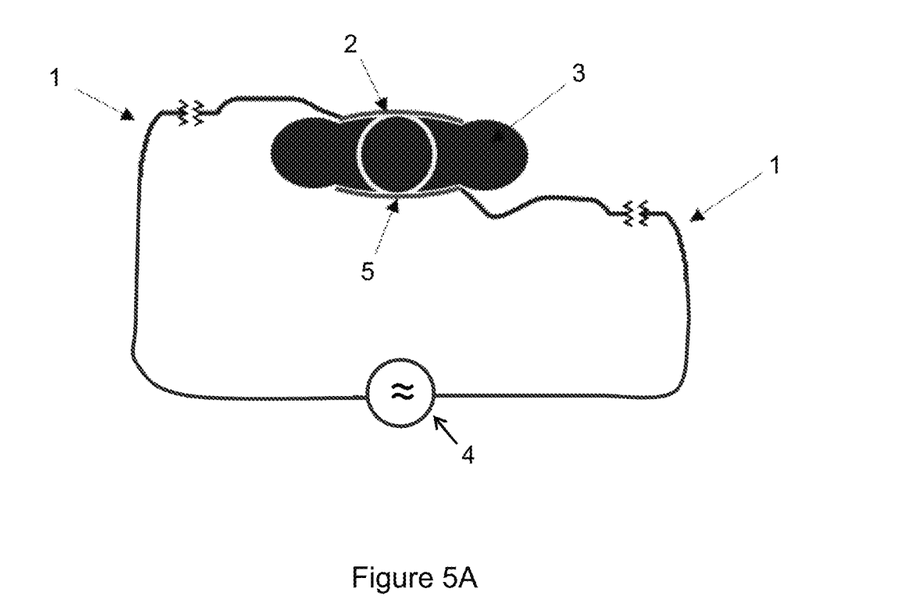
FIG. 5A shows an example of the inventive electromagnetic energy transfer means (electrode) made of a conductive material in form of a coating or in form of a metallic net and a counter electrode both applied to the uneven surface of the patient's body. In symmetric case two actually oppositely "charged" electrodes make the capacitor, in asymmetric case a grounded counter electrode is used.

FIG. 5A shows an alternate example of a hyperthermia device. Similar to FIG. 1, the device includes an RF electrode 2 positioned opposite to a counter electrode 5 so that the patient 3 becomes part of the condenser circuit when the current is applied to the electrodes. Both electrodes (2, 5) are coupled to the same RF source 4 via cables 1.

Figure 5B:
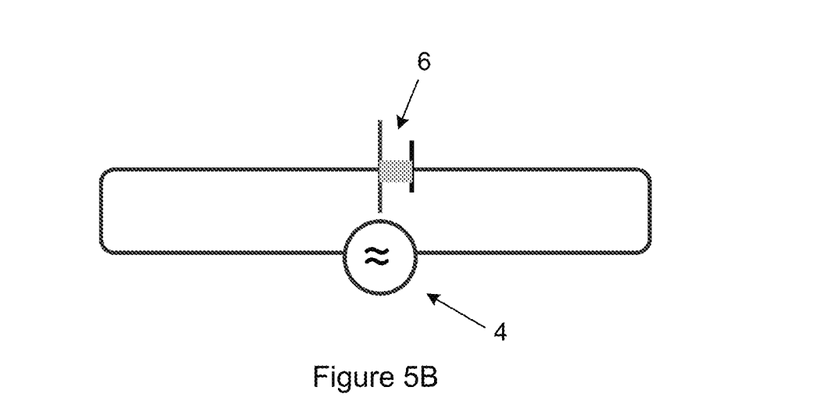
FIG. 5B illustrates that the electromagnetic energy transfer means (electrode) together with the patient's body and the counter electrode are arranged as a condenser, so that the electromagnetic energy transfer means is part of a condenser.

FIG. 5B illustrates that the electromagnetic energy transfer means (electrode) together with the patient's body and the counter electrode are arranged as a condenser 6, so that the electromagnetic energy transfer means is part of a condenser.

The RF-electrode and most preferably also the counter-electrode are defined as the electromagnetic energy transfer means so that the embodiments are also directed to said electromagnetic energy transfer means which is part of the condenser for directing energy to a target, the electromagnetic energy transfer means including at least one conductive metal electrode material in form of a coating or a metallic net,
  wherein at least one conductive metal electrode material layer is coated onto the surface of a flexible carrier,
  and wherein the coated flexible carrier is porous and allows the movement of water through the coated flexible carrier or wherein the at least one conductive metal electrode material constructs a flexible carrier in form of a metallic net,
and wherein the flexible carrier is porous and allows the movement of water through the flexible carrier,
and wherein the at least one conductive metal electrode material in form of a coating or a metallic net is not isolated.

Since the hyperthermia device or hyperthermia arrangement uses the condenser arrangement, the electrode and the counter electrode should not be isolated from the skin or skin surface where the electrode and counter electrode is attached to or which is covered by the electrode or the counter electrode respectively.

The direct connection of the electrode and the counter electrode to the skin allows direct current flow through the patient which allows the applied voltage to be kept lower than any earlier solutions. In earlier capacitive solutions the electrodes were highly isolated by water boluses (preferable made from silicone). These highly isolating layers were part of the circuit like serial impedances. The high impedance requests high voltage at definite power, because $U^2=P*Z$, where U is the voltage P is the power and Z is the actual impedance. The current in the same case is low ($I^2=P/Z$, where I is the current). If the isolating layers are eliminated the impedance could be lowered drastically, so that the voltage square lowers and the current square increases proportionally, in order to improve the energy-transfer and suppress the radiation loss. This again is important for focusing the heat at the diseased tissue such as a tumor and to avoid burning of the healthy tissue. At the beginning of our development of the hyperthermia device including the electromagnetic energy transfer means, the voltage at 150 W was about 85 V, while now in the same conditions we are at 27 V. The 3-times dropped voltage increased the current also three times, at the same power. The heating efficacy increased very much. According to our measurements, keeping 42° C. in a HT29 (human colorectal xenograft) tumor of a mouse 15 W was necessary in the bolus system, while in the new system the same size tumor keeping the same 42° C. requested only 1.5 W. This is a ten times power-efficacy. The advantage is not only this, but also the lower voltage creates less scattered capacity to the environment, so that the accuracy of the power control is better.

Moreover said direct connection of the electrode and the counter electrode to patient's skin makes any cooling device, cooling bolus or cooling apparatus for skin cooling of the area where the electrodes are superfluous.

The electrode is connected by a single cable to the RF source and the counter electrode is also connected by a single cable to the RF source which makes the complete condenser arrangement quite easy and enhances the wearing comfort of the patient.

Also very important in comparison to an antenna arrangement is that the electrode and also the counter electrode are equipotential, i.e. each electrode (the electrode and the counter electrode) have the same potential in or over their complete surface. The non-equipotent surfaces of, for instance, an antenna arrangement as described in U.S. Pat. No. 6,330,479 will generate current in the electrode, heating up the electrode itself, and produce safety problems. This problem is completely avoided by the condenser arrangement, where not the at least two electrodes are heated rather than the medium in between these at least two capacitive electrodes and the medium in between the electrodes is the diseased tissue of the patient which is normally not in direct vicinity of the electrode surface.

Thus the electrode and preferably also the counter electrode or the other oppositely charged capacitive electrode includes a flexible, water-permeable, gas-permeable, conductive, textile-like metallic net or flexible, water-permeable, gas-permeable, textile-like material or carrier which is coated with a conductive metal electrode material. Said electrodes look like a piece of fabric or a piece of cloth which can have any size and which is able to cover a certain part of the body like clothes.

Regardless the size of the electrode and regardless how said electrode is fixed or attached to a certain body area, it has the same potential throughout its whole surface.

The hyperthermia device is especially useful for the heat treatment of deep tissue which is up to 10 cm within patient's body.

The term "hyperthermia" as used herein refers to heating up a target higher than the environment equilibrium temperature. Thus the afore-mentioned device including the energy transfer means is not only suitable to treat humans or animals but also for the hyperthermia treatment of any living and non-living targets and can be used in RF welding, soldering and gluing or in keeping any kind of target material warm such as gases, solids, fluids, liquids, such as dielectric materials.

The coated surface or the coated sheet of flexible material allows the movement of air and water/aqueous solution through the material. The coated sheet of flexible material allows the movement of fluid through the material.

The coated sheet of flexible material can form a cylinder. The coated sheet of flexible material can also be folded.

Moreover in a preferred embodiment the flexible coated carrier or the flexible metallic net is arranged in a way that it includes multiple positive and negative sections or multiple positive and negative electrodes which are arrayed in an alternating positive and negative section or electrode arrangement.

Said alternating positive and negative section or electrode arrangement can be in the form of a matrix arrangement, a plurality of matrix arrangements, a concentric ring arrangement or a plurality of concentric ring arrangements. The matrix arrangement can be in form of a chess board arrangement and the concentric ring arrangement can be in form of a single structure of concentric rings or a sphere packing of a plurality of concentric ring arrangements.

Such arrangements are especially preferred for the treatment of surface tissue such as dermis, epidermis or subcutaneous tissue. Moreover all arrangements disclosed herein are useful to treat joints or cartilage tissue.

The number of electrode pairs in these arrangements is not limited but is normally between 1 and 50 and more preferably 1, 2, 3, 4, 5, 6, 8, 9, 12, 16, 20, 24, 25, 28, 30, 32, 34, 36, 38, 40, 42, 49.

Moreover in these multiple electrode arrangements it is preferred that at least one of these electrodes is used as measurement electrode while all other electrodes are used as treatment electrodes.

The size of the electrode is not limited, but of course is adjusted to the application of interest, i.e. for instance to the body part that should be treated or to the shape of a cavity that should be warmed or kept at a temperature achievable by hyperthermia treatment.

Another aspect is the use of the electric field capacitive coupled energy transfer means including conductive metal electrode material, wherein at least one conductive metal electrode material layer is coated onto a sheet of flexible material, and wherein the coated sheet of flexible material is porous to provide an improved method of hyperthermia treatment for the treatment of a target tissue of any living or not-living objects.

Tumor cells are preferentially sensitive to heat in comparison to normal tissue. Thus, the hyperthermia device can be used for treatment and/or prophylaxis of epithelial cancers. All types of cancers that occur in surface tissues can be treated using the device, for example, basal cell carcinoma, squamous cell carcinoma, melanoma, Kaposi sarcoma, cutaneous lymphomas, skin adnexal tumours, soft tissue sarcomas of the dermis, soft tissue sarcomas subcutaneous tissue, Merkel cell carcinoma, dermatofibrosarcoma protuberans (DFSP) and angiosarcoma. The electric field capacitive coupled energy transfer means can also be used in combination with other forms of cancer therapy, for example chemotherapy, radiotherapy and surgery.

The electric field capacitive coupled energy transfer means can also be used for the treatment and/or prophylaxis of joint and articular diseases and conditions, for example, rheumatoid arthritis, rheumatism, gout, ankylosing spondylitis and lupus.

The electric field capacitive coupled energy transfer means can also be used for the treatment and/or prophylaxis of respiratory diseases and conditions, for example, asthma, allergic rhinitis and the common cold.

The electric field capacitive coupled energy transfer means can also be used to enhance surface microcirculation. This is useful to treat fatigue by detoxification of the treated area.

The electric field capacitive coupled energy transfer means can also be used for the treatment of muscle injury in humans or animals.

The electric field capacitive coupled energy transfer means can also be used to enhance surface microcirculation and heat surface tissue to prevent muscle spasms and muscle injury in humans or animals.

The electric field capacitive coupled energy transfer means can also be used for cosmetic purposes, for example, cellulite treatment, fat reduction and tissue lifting.

The field capacitive coupled energy transfer means and method provides the following significant advantages over prior art electric field coupled energy transfer means and methods.

By the use of the electric field capacitive coupled energy transfer means energy can be delivered to difficult to treat surface areas or to large surface areas.

Further the electric field capacitive coupled energy transfer means provides improved patient safety and comfort due to the porosity of the energy transfer means allowing the exchange of heat and fluids.

Also the electric field capacitive coupled energy transfer means provides improved energy transfer in comparison to a conventional bolus electrode due to the high inductive coupling and low impedance.

In summary, embodiments described herein are directed to a deep-heating of diseased tissue hyperthermia device using radiofrequency in a condenser arrangement of at least two electrodes which are equipotential over their total surface, not isolated against to skin where they are attached to and which do not have any cooling system or cooling bolus and which are each connected through a single cable to a radiofrequency source using RF-current of typically 13.56 MHz. The one or at least one electrode (RF-electrode) and/or the one counter or at least one counter electrode or the other capacitive electrode or the at least one other capacitive electrode are the electromagnetic energy transfer means which are part of a condenser for directing energy to a target, the electromagnetic energy transfer means including at least one conductive metal electrode material in form of a coating or a metallic net, wherein at least one conductive metal electrode material layer is coated onto the surface of a flexible carrier, and wherein the coated flexible carrier is porous and allows the movement of water through the coated flexible carrier or wherein the at least one conductive metal electrode material constructs a flexible carrier in form of a metallic net, and wherein the flexible carrier is porous and allows the movement of water through the flexible carrier, and wherein the at least one conductive metal electrode material in form of a coating or a metallic net is not isolated.

The electrode and preferably also the counter-electrode or the other oppositely charged capacitive electrode follows well the shape of the body, giving perfect contact all over the covered surface, i.e. the covered skin where the electrode(s) are put on or attached to or which is covered by said electrode(s).

The arrangement of these flexible conductive textile-like electrode and preferably flexible conductive textile-like counter electrode or capacitive electrode substitutes the very complicated and not-easy-use bolus systems, makes it possible to apply any shape of these electrodes, which fit to the treated lesion best (e.g. head, leg, breast, fundament etc.), solves the generally problematic cooling of the body surface, keeps the applied voltage low and the applied current high to improve the energy-transfer and suppress the radiation loss.

Moreover this arrangement makes the use of large electrodes possible without large water weight, for multilocal treatments (e.g. for distant metastases) and eliminates the isolator of the bolus materials and the other layers in the old common applicator by applying direct electrode contact to the skin surface. Finally the electrodes of the arrangement or of the hyperthermia device are easy and simple to produce and make the treatment procedure also easier and better tolerable by the patients.

EXAMPLES

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1

Treatment of Liver Metastases from Colorectal Primary Tumor

A textile like structure of 400 $cm^2$ including polyamide fibers is activated by palladium-layer and coated with a first nickel boride layer via electroless coating and thereafter a silver layer is applied also via electroless coating.

Said electromagnetic energy transfer means in form of a porous, flexible and coated polyamide textile is used in a hyperthermia arrangement. The coated textile like structure is placed below a patient smoothly attached to his back and on another one smoothly on the patient's chest. All the cancer-lesions which were treated till now by bolus-like systems could be handled by this new and inventive solution better and safer. The lesions in this example are liver metastases from colorectal primary tumor. This very common cancer is one of the most problematic to treat, due to the fatty layer between the liver and the skin.

Both coated textile like polyamide structures are connected to a power supply. The patient is heated by deep hyperthermia with 70 W (13.56 MHz, sinusoidal current, capacitive coupling, RF-current flows through the patient), providing 252 kJ energy (duration is one hour). Patient tolerated the treatment well, and reported later an improvement of the quality of life. The treatment is repeated twice a week by five weeks.

Example 2

Lung-Cancer Treatment

The same arrangement as in example 1 was used for the treatment of lung cancer. The hyperthermia treatment is a complementary method so it was applied in combination with conventional cancer therapies. In the given lung-cancer case a common chemotherapy with Gemzitabine was applied.

The additional hyperthermia treatment supported the common chemotherapy remarkably and prolonged patient's expectation of life.

Example 3

Treatment of Gall-Bladder and Intrahepatic Bile-Path Cancer

Another application is by the same arrangement, RF-current (4000 cm$^2$, 13.56 MHz, 60 W), flows through the patient between the electrodes. The treated area is the gall-bladder and the intrahepatic bile-path. The heating of the patient by the electrode-tissues, that means by the electrodes in form of a cloth or fabric or piece of textile which makes the electromagnetic energy transfer, are smoothly attached and are properly matched to the curvatures of the patient's body. The flexible energy transfer means, i.e. the metallic net or the coated carrier heats the target area to about 40° C.

The duration of treatment session was one hour in both cases.

Example 4

Treatment of Rheumatoid Arthritis

Patients suffering from rheumatoid arthritis. The electrodes are conductively heated by direct flow of electric current through them (not through the patient). The heated electrodes heated up the body-part when they were placed over the joint. The hyperthermia treatment was applied for one hour per day and three times a week in period of 2 months. The applied energy was 10-20 W, 50 Hz AC-frequency and symmetrically arranged 10×10 cm rounded-square electrodes. Patient had reported good subjective reaction even after the first treatment, and considerable improvement of the quality of life after the course.

Example 5

Asthma Treatment

A textile like structure of 1,100 cm$^2$ including polyamide fibers is activated by palladium layer and coated with a first nickel boride layer via electroless coating and thereafter a silver layer is applied also via electroless coating.

Said electromagnetic energy transfer means in form of a porous, flexible and coated polyamide textile is used in a hyperthermia arrangement. The coated textile like structure is placed below a patient smoothly attached to his back and on another one smoothly on the patient's chest, over his lung-lobes, covering the full area smoothly.

Both coated textile like polyamide structures are connected to a power supply. The patient is heated by deep hyperthermia with 150 W (13.56 MHz, sinusoidal current, capacitive coupling, RF-current flows through the patient), providing 350 kJ energy (duration is one hour). Patient suffering from asthma tolerated the treatment well, and reported later a definite and drastic reducing the till necessary steroid drugs. (The regular use was reduced to sporadic time-to time if it was necessary.) The treatment is repeated twice a week by two weeks.

Example 6

Cellulite Treatment

The cellulite treatment uses the deep-heat and the restructuring facility of the hyperthermia. This type of heating is available in many commercial devices but these new electrodes with RF-frequency activation make effective deep heat, large area (practically it could be confectionized on the patient's shape) and absolute smooth, flexible fitting to the non-smooth skin surface. The example showed the electrode was placed on the patient's upper-limb (up to the groin region) oppositely 10×10 cm rounded square, and was applied 35 W for 30 min. The cellulite surface became smoother. The process was repeated three-times a week during two weeks, and the result was satisfactory reducing of the cellulite structure.

Example 7

Fat Reduction

Similarly to the cellulite treatment it has also many commercial availabilities on the market, but these new electrodes give new facilities. The electrode and the treatment was the same like in Example 6, only the treatment was repeated every day during a week. The result was satisfactory, the circumflex of the limb was shrinking by 4%.

Further modifications and alternative embodiments of various aspects of the invention will be apparent to those skilled in the art in view of this description. Accordingly, this description is to be construed as illustrative only and is for the purpose of teaching those skilled in the art the general manner of carrying out the invention. It is to be understood that the forms of the invention shown and described herein are to be taken as examples of embodiments. Elements and materials may be substituted for those illustrated and described herein, parts and processes may be reversed, and certain features of the invention may be utilized independently, all as would be apparent to one skilled in the art after having the benefit of this description of the invention. Changes may be made in the elements described herein without departing from the spirit and scope of the invention as described in the following claims.

What is claimed is:

1. An electromagnetic energy transfer means for use in hyperthermia therapy, the electromagnetic energy transfer means comprising at least two conductive metal electrode materials in a condenser arrangement,
  wherein the at least two conductive metal electrode materials comprise: a metallic coating on a surface of a flexible carrier forming a coated flexible carrier, or a woven structure of metallic fibers forming a metallic net,
  wherein the coated flexible carrier or metallic net is porous and allows the movement of water and perspiration there through;
  wherein the coated flexible carrier or metallic net is not insulated from a patient's skin during use and wherein the electromagnetic energy transfer means uses radiofrequencies in the range of 10 KHz to 50 MHz; and
  wherein the coated flexible carrier or the metallic net comprises multiple positive and negative sections or multiple positive and negative electrodes which are arrayed in an alternating positive and negative section arrangement or positive and negative electrode arrangement;
  wherein the electromagnetic energy transfer means is a capacitive coupled energy transfer means that is equipotential over its total surface, and
  wherein the woven structure of metallic fibers forming a metallic net is a textile consisting of a plurality of single fibers wherein one set of the single fibers extends along the complete length of the textile in a substantially parallel manner while the other set of fibers is arranged in a substantially parallel manner diagonal to the first set of fibers.

2. The electromagnetic energy transfer means of claim 1, wherein the conductive metal electrode material is selected from silver, nickel, copper, gold and alloys containing silver, nickel, copper or gold.

3. The electromagnetic energy transfer means of claim 1, wherein the coated flexible carrier is selected from a textile, a plastic, polyamide, poly-ε-caprolactone, poly-para-dioxanones, polyanhydrides, polyhydroxymethacrylates, fibrin, polyetherester, PEG, poly(butylene terephthalates), polycarbonates, poly(N-vinyl)-pyrrolidone, polyvinylalcohols, polyesteramides, polyethyleneoxide, polypropyleneoxide, polyurethanes, fibrinogen, starch, collagen, zein, casein, β-cyclodextrins, polyacrylates, polyacrylamide, polyimides, polyethylene, polypropylene, polytetrafluoroethylene, fluorosilicones, rayon, polysulphones, silicones, polysiloxanes, polyvinyl halogens and copolymers or mixtures of these substances.

4. The electromagnetic energy transfer means of claim 1, wherein the coated flexible carrier or the metallic net allows the movement of air therethrough.

5. The electromagnetic energy transfer means of claim 1, wherein the coated flexible carrier or the metallic net allows the movement of fluid therethrough.

6. The electromagnetic energy transfer means of claim 1, wherein the coated flexible carrier or the metallic net can form a cylinder or any other form adapted to any shape of a human or animal body.

7. The electromagnetic energy transfer means of claim 1, wherein the coated flexible carrier or the metallic net can be folded.

8. The electromagnetic energy transfer means of claim 1, wherein the electromagnetic energy transfer means does not comprise a cooling system or a cooling device or a cooling bolus.

9. The electromagnetic energy transfer means of claim 1, wherein the electromagnetic energy transfer means is connected to a radiofrequency source through a single cable.

10. The electromagnetic energy transfer means of claim 1, wherein the at least one conductive metal electrode material in the form of a coating or a metallic net is positioned opposite to at least one counter-electrode or one oppositely charged capacitive electrode.

11. The electromagnetic energy transfer means of claim 1, wherein the electromagnetic energy transfer means is part of a condenser.

12. Hyperthermia device comprising the electromagnetic energy transfer means as defined in claim 1.

13. A method for the prevention and treatment of cancer, rheumatoid arthritis, rheumatism, gout, ankylosing spondylitis, lupus, asthma, allergic rhinitis, common cold, fatigue by detoxification of the treated area, muscle spasms, muscle injury, cellulite treatment, fat reduction and tissue lifting in a patient comprising:
  applying radiofrequencies in the range of 10 KHz to 50 MHz using a hyperthermia device comprising an electromagnetic energy transfer means as defined in claim 1.

14. A method of using electromagnetic energy transfer for cosmetic purposes, for fat reduction for cosmetic purposes, for tissue lifting or for prophylaxis and treatment of cellulite in a patient comprising
  applying radiofrequencies in the range of 10 KHz to 50 MHz using a hyperthermia device comprising an electromagnetic energy transfer means as defined in claim 1.

* * * * *

UNITED STATES PATENT AND TRADEMARK OFFICE
CERTIFICATE OF CORRECTION

PATENT NO. : 9,636,495 B2  
APPLICATION NO. : 12/863418  
DATED : May 2, 2017  
INVENTOR(S) : Szasz et al.

Page 1 of 1

It is certified that error appears in the above-identified patent and that said Letters Patent is hereby corrected as shown below:

In the Assignee:

Please delete "Oncother Kft" and substitute therefor --Oncotherm Kft--.

Signed and Sealed this  
Eleventh Day of July, 2017

Joseph Matal  
*Performing the Functions and Duties of the*  
*Under Secretary of Commerce for Intellectual Property and*  
*Director of the United States Patent and Trademark Office*